(12) United States Patent
Paulsson et al.

(10) Patent No.: US 8,692,033 B2
(45) Date of Patent: Apr. 8, 2014

(54) PRODUCTION OF 1,6-HEXANEDIOL

(75) Inventors: Christoffer Paulsson, Eslov (SE); Katri Nikkila, Espoo (FI); Hakan Bjornberg, Angelholm (SE)

(73) Assignee: Perstorp AB, Perstorp (SE)

( * ) Notice: Subject to any disclaimer, the term of this patent is extended or adjusted under 35 U.S.C. 154(b) by 0 days.

(21) Appl. No.: 13/809,132

(22) PCT Filed: Jul. 11, 2011

(86) PCT No.: PCT/SE2011/000131
§ 371 (c)(1),
(2), (4) Date: May 15, 2013

(87) PCT Pub. No.: WO2012/008894
PCT Pub. Date: Jan. 19, 2012

(65) Prior Publication Data
US 2013/0225875 A1    Aug. 29, 2013

(30) Foreign Application Priority Data
Jul. 13, 2010    (SE) ....................................... 1000760

(51) Int. Cl.
C07C 27/04    (2006.01)

(52) U.S. Cl.
USPC .......................................................... 568/864

(58) Field of Classification Search
None
See application file for complete search history.

(56) References Cited

FOREIGN PATENT DOCUMENTS

JP        06345674 A  *  12/1994

OTHER PUBLICATIONS

Chemical Engineering Science 59 (2004) 5479-5485; Real-Time In Situ ATR-FTIR Analysis of the Liquid Phase Hydrogenation of . . . ; Gerben M. Hamminga.

* cited by examiner

*Primary Examiner* — Sudhakar Katakam
(74) *Attorney, Agent, or Firm* — Novak Druce Connolly Bove + Quigg LLP

(57) ABSTRACT

The present invention refers to a process for hydrogenation of caprolactone and/or its oligomers or polymers to 1,6-hexanediol. The process is performed in liquid phase at a pressure between 100 and 350 bar and is performed in the presence of a catalytically effective amount of at least one catalyst comprising Cu, Mn, Al, Cr, Zn, Ba and/or Zr.

8 Claims, No Drawings

PRODUCTION OF 1,6-HEXANEDIOL

The present invention refers to a process for hydrogenation of caprolactone and/or its oligomers or polymers to 1,6-hexanediol. Said process is performed in liquid phase at a pressure between 100 and 350 bar and is performed in the presence of a catalytically effective amount of at least one catalyst comprising Cu, Mn, Al, Cr, Zn, Ba and/or Zr.

1,6-hexanediol is a useful starting material for producing polyurethanes, polyester-type plasticizers, unsaturated polyesters, 1,6-hexanediol diacrylate etc. It is known from for example U.S. Pat. No. 6,288,286 that 1,6-hexanediol can be prepared from a carboxylic acid mixture obtained as by-product in the oxidation of cyclohexane to cyclohexanone/cyclohexanol. The mixture of by-products from this reaction include adipic acid, 6-hydroxycaproic acid and small amounts of 1,4-cyclohexanediols. These carboxylic acids are esterified with a low molecular weight alcohol and the resulting esters are reacted with hydrogen in the presence of a catalyst for hydrogenation. This process is disadvantageous in that a separate esterification step is required, which means that the process has to be conducted in two different reactors. A more straightforward, one-pot process for producing 1,6-hexanediol would be desirable.

In U.S. Pat. No. 5,981,769 a process for production of 1,6-hexanediol in gas phase is described. The process, however, is cumbersome since it contains 14 separate steps. U.S. Pat. No. 6,008,418 describes a process for preparation of 1,6-hexanediol with a purity of 99% wherein 10 steps, however the process is still cumbersome since a separate purification step is required to reach such a high purity.

German Patent application no. 2060548 describes a process for preparation of 1,6-hexanediol in which purification of the product is carried out using a crystallization step. The purity of the resulting product is greater than 99.5% but the yield is well below 50%. The Japanese laid open publication S64-85938 discloses hydrogenating dimethyl adipate or diethyl adipate to hexanediol in the gas phase in the presence of a copper-chromite catalyst at 160-250° C. and 10-70 atm. and diester hydrogen molar ratios of 1-100 to 1-590. A selectivity for 1,6-hexanediol of about 98% is achieved in only 1 of 11 operative (embodiment, no. 6) examples. However, the employed hydrogen diester molar ratio of 457 leads to very high energy costs. Of the processes for preparation of 1,6-hexanediol above, none uses caprolactone as a reactant. British Patent no. 1059598 discloses a process in which esters are converted into their monohydric or dihydric corresponding alcohols. One embodiment example describes a process in which ε-caprolactone is converted into 1,6-hexanediol at a purity of 89%. In the British Patent no. 1120427 a process in which a polyester of lactone-type is converted to 1,6-hexanediol at a selectivity of less than 90% in liquid phase is described.

The process according to the present invention provides advantages over the processes described above due to the fact that a high selectivity, as high as 99.7% when monomer raw material and 97.8% when a mixture of oligomers and polymers of caprolactone are used as raw material, under optimal conditions at the most preferred pressure interval of 260 to 300 bar, are obtained without any separate purification step and that the process at the same time is carried out in one process stage requiring only a single reactor as process equipment. Due to the decrease in process stages and process equipment needed, the energy requirements for the process according to the present invention is greatly reduced whilst maintaining a conversion of caprolactone and/or its oligomers or polymers raw material to the product 1,6-hexanediol of 99% to 100%. Caprolactone oligomers and caprolactone polymers are herein defined as a substance containing 2 to 3 caprolactone monomer units and a substance containing at least 4 caprolactone monomer units, respectively. Caprolactone is herein taken to be caprolactone monomer unless otherwise stated.

The present invention refers to a simplified process for hydrogenation of caprolactone and/or its oligomers or polymers to 1,6-hexanediol. The process is performed in liquid phase at a pressure between 100 and 350 bar and in the presence of a catalytically effective amount of at least one catalyst comprising Cu, Mn, Al, Cr, Zn, Ni, Pd, Ba and/or Zr.

The catalyst can be present as one or more oxides, for example CuO, or one or more elemental metals or as a combination of one or more oxides and one or more elemental metals. The present invention exhibits good results and high selectivity for this kind of reaction, indicating that it is likely that the catalysts would give good results also in the process described in the present invention. In one preferred embodiment the catalyst is CuO.

The catalyst is preferably in the form of tablets, powder or extrudate depending on the type of reactor. Batch, semi-batch or fixed bed reactors are preferably used for the process according to the invention. For batch and semi-batch reactors the catalytically effective amount of the catalyst is preferably 0.1 to 25%, more preferably 0.1 to 20% and even more preferably 0.1 to 15% by weight of the raw material for catalysts in tablet form and preferably 0.1 to 8%, more preferably 0.1 to 6% and even more preferably 0.1 to 4% by weight of the raw material for catalysts in powder form. For fixed-bed reactors the catalytically effective amount of the catalyst preferably corresponds to a liquid hourly space velocity (LHSV) value between 0.01 and 7/h, more preferably between 0.05 and 5/h.

According to preferred embodiments of the present invention, the catalyst further comprises a promoter. The promoter is preferably, but not limited to, $MnO_2$, BaO, MgO, ZnO, FeO, $Fe_2O_3$, $Fe_3O_4$ or a mixture thereof.

The catalyst is preferably supported on a carrier such as $Al_2O_3$, $SiO_2$, $TiO_2$, activated carbon, $Cr_2O_3$, ZnO or CaO.

The process according to the present invention is preferably carried out as a cascade reaction process in one single reactor (also known as a one-pot process). Caprolactone monomers, oligomers or polymers and/or a mixture thereof are preferably used as raw material in the process according to the invention. The caprolactone polymer preferably contains on average at most 12, more preferably at most 10 and most preferably at most 6 caprolactone monomer units.

According to a preferred embodiment of the present invention, the pressure during said process is preferably kept between 160 and 320 bar, more preferably between 220 and 310 bar and even more preferably between 260 and 300 bar.

According to a preferred embodiment of the present invention, the temperature during said process is between 150-280° C. and preferentially between 180-240° C.

According to one embodiment of the present invention, said process is performed in the presence of at least one solvent. This solvent can be a single solvent, a combination of solvents or a combination of solvents and co-solvents.

According to one embodiment of the present invention said at least one solvent is selected from the group consisting of a $C_1$-$C_6$ branched or unbranched alcohol such as methanol, ethanol, isopropanol, n-propanol, iso-butanol, 1,6-hexanediol, ethyleneglycol or propyleneglycol, a $C_1$-$C_6$ branched or unbranched ether such as 1,3-dioxolane, tetrahydrofuran, dioxane, tetraethylene glycol, dimethylether, diethylether, methyl tert-butylether, ethyleneglycol dimethylether, water or a combination thereof. Experiments have shown that n-butanol is not a suitable solvent for the process according to the present invention.

In a preferred embodiment of the present invention, the process is solvent-free, that is, 1,6-hexanediol which is the reaction product is in the process also used as solvent in the process, resulting in high purity 1,6-hexanediol.

In one embodiment of the present invention, the product mixture remaining after recovery of 1,6-hexanediol is recirculated to the reactor and used as feed material in the process.

The present invention is further explained with reference to the enclosed Embodiment Examples, which are to be constructed as illustrative and not limiting in any way.

Example 1-3 illustrates the invention and refers to a process in which ε-caprolactone is hydrogenated to 1,6-hexanediol using different catalysts in tablet form at a pressure of 160-175 bar.

Example 4-6 illustrates the invention and refers to a process in which ε-caprolactone is hydrogenated to 1,6-hexanediol, using different solvents.

Example 7-8 illustrates the invention and refers to a process in which ε-caprolactone is hydrogenated to 1,6-hexanediol at a pressure of 230-250 bar using isobutanol and 1,6-hexanediol as solvents.

Example 9-10 illustrates the invention and refers to a process in which ε-caprolactone is hydrogenated to 1,6-hexanediol at pressures of 270-300 and using isobutanol and methanol as solvents.

Example 11-12 illustrates the invention and refers to a process in which a mixture of caprolactone oligomers and polymers are hydrogenated to 1,6-hexanediol at different pressures.

Example 13 is a comparative example outside the scope of the invention and refers to a process in which ε-caprolactone is hydrogenated to 1,6-hexanediol, using n-butanol as a solvent and a pressure of 160-175 bar.

Example 14-15 are comparative examples outside the scope of the invention and refers to processes in which ε-caprolactone is hydrogenated to 1,6-hexanediol at pressures of 75-90 bar.

EXAMPLE 1

Hydrogenation of ε-caprolactone to 1,6-hexanediol was performed in a reactor provided with agitation. ε-Caprolactone was fed in a concentration of about 50 vol % of the solvent isobutanol over a catalyst T-4489 (56% CuO, 34% $Al_2O_3$ and 10% $MnO_2$) in tablet form from Süd-Chemie. The temperature during the experiment was 220° C. and the pressure was kept at 160-175 bar. The reaction was allowed to run for 5 hours. 1,6-hexanediol was recovered from a product mixture of 1,6-hexanediol, ε-caprolactone and some oligomers of caprolactone. The product was analysed by standard GC-procedures. The caprolactone conversion and the selectivity for 1,6-hexanediol are seen in Table 1.

EXAMPLE 2

The procedure described in Example 1 was repeated, with the difference that G-99-B-0 (47% CuO, 46% $Cr_2O_3$, 4% $MnO_2$ and 2% BaO) in tablet form from Süd-Chemie was used as catalyst. The caprolactone conversion and the selectivity for 1,6-hexanediol are seen in Table 1.

EXAMPLE 3

The procedure described in Example 1 was repeated, with the difference that T-2130 (33% CuO, 66% ZnO) in tablet form from Süd-Chemie was used as catalyst. The caprolactone conversion and the selectivity for 1,6-hexanediol are seen in Table 1.

EXAMPLE 4

The procedure described in Example 2 was repeated, with the difference that the catalyst was in powder form. The caprolactone conversion and the selectivity for 1,6-hexanediol are seen in Table 1.

EXAMPLE 5

The procedure described in Example 4 was repeated, with the difference that isopropanol was used as solvent. The caprolactone conversion and the selectivity for 1,6-hexanediol are seen in Table 1.

EXAMPLE 6

The procedure described in Example 4 was repeated, with the difference that methanol was used as solvent. The caprolactone conversion and the selectivity for 1,6-hexanediol are seen in Table 1.

EXAMPLE 7

The procedure described in Example 4 was repeated, with the difference that 1,6-hexandediol was used as solvent and that the pressure was kept at 230-250 bar. The caprolactone conversion and the selectivity for 1,6-hexanediol are seen in Table 1.

EXAMPLE 8

The procedure described in Example 4 was repeated, with the difference that the pressure was kept at 230-250 bar. The caprolactone conversion and the selectivity for 1,6-hexanediol are seen in Table 1.

EXAMPLE 9

The procedure described in Example 4 was repeated, with the difference that the pressure was kept at 280-300 bar. The caprolactone conversion and the selectivity for 1,6-hexanediol are seen in Table 1.

EXAMPLE 10

The procedure described in Example 6 was repeated, with the difference that the pressure was kept at 270-290 bar and that T-4489 (56% CuO, 34% $Al_2O_3$ and 10% $MnO_2$) in tablet form from Süd-Chemie was used as catalyst. The caprolactone conversion and the selectivity for 1,6-hexanediol are seen in Table 1.

EXAMPLE 11

Hydrogenation of caprolactone oligomers to 1,6-hexanediol was performed in a reactor provided with agitation. A mixture of oligomers and polymers of caprolactone with a mean molecular weight of 1250 g/mol was fed in a concentration of about 50 vol % of the solvent isobutanol over a catalyst G-99-B-0 (47% CuO, 46% $Cr_2O_3$, 4% $MnO_2$ and 2% BaO) in powder form from Süd-Chemie. The temperature during the experiment was 220° C. and the pressure was kept at 160-175 bar. The reaction was allowed to run for 5 hours. 1,6-hexanediol was recovered from a product mixture of 1,6-hexanediol, ε-caprolactone and some oligomers of caprolactone. The product was analysed by standard GC-procedures. The caprolactone conversion and the selectivity for 1,6-hexanediol are seen in Table 1.

EXAMPLE 12

The procedure described in Example 11 was repeated, with the difference that the pressure was kept at 230-250 bar. The caprolactone conversion and the selectivity for 1,6-hexanediol are seen in Table 1.

EXAMPLE 13

Comparative Example

The procedure described in Example 4 was repeated, with the difference that n-butanol was used as solvent. The caprolactone conversion and the selectivity for 1,6-hexanediol are seen in Table 1.

EXAMPLE 14

Comparative Example

The procedure described in Example 1 was repeated, with the difference that the pressure was kept at 75-90 bar and the reaction time was 8 h. The caprolactone conversion and the selectivity for 1,6-hexanediol are seen in Table 1.

EXAMPLE 15

Comparative Example

The procedure described in Example 14 was repeated, with the difference that a 5% $Ru/Al_2O_3$ catalyst in tablet form was used. The caprolactone conversion and the selectivity for 1,6-hexanediol are seen in Table 1.

It can be concluded from these embodiment examples that using a Cu-based catalyst the process according to the present invention has a selectivity for 1,6-hexanediol as high as 99% at the most preferred pressure interval of 260 to 300 bar.

TABLE 1

Caprolactone conversion and selectivity for 1,6-hexanediol using caprolactone monomer, oligomer and polymer as raw material.

| Example no. | Metal | Carrier | Promoter | Form of catalyst | Pressure (bar) | Temperature (° C.) | Solvent | Conversion (%) | Selectivity (%) |
|---|---|---|---|---|---|---|---|---|---|
| Monomer raw material | | | | | | | | | |
| Example 1 | Cu | $Al_2O_3$ | $MnO_2$ | tablet | 160-175 | 220 | isobutanol | 93.1 | 85.2 |
| Example 2 | Cu | $Cr_2O_3$ | $MnO_2$, BaO | tablet | 160-175 | 220 | isobutanol | 82.4 | 72.3 |
| Example 3 | Cu | ZnO | | tablet | 160-175 | 220 | isobutanol | 99.8 | 97.4 |
| Example 4 | Cu | $Cr_2O_3$ | $MnO_2$, BaO | powder | 160-175 | 220 | isobutanol | 99.6 | 84.1 |
| Example 5 | Cu | $Cr_2O_3$ | $MnO_2$, BaO | powder | 160-175 | 220 | isopropanol | 98.0 | 64.4 |
| Example 6 | Cu | $Cr_2O_3$ | $MnO_2$, BaO | powder | 160-175 | 220 | methanol | 86.6 | 65.4 |
| Example 7 | Cu | $Cr_2O_3$ | $MnO_2$, BaO | powder | 230-250 | 220 | 1,6-hexanediol | 99.7 | 96.7 |
| Example 8 | Cu | $Cr_2O_3$ | $MnO_2$, BaO | powder | 230-250 | 220 | isobutanol | 99.8 | 97.3 |
| Example 9 | Cu | $Cr_2O_3$ | $MnO_2$, BaO | powder | 280-300 | 220 | isobutanol | 100 | 99.3 |
| Example 10 | Cu | $Al_2O_3$ | $MnO_2$ | tablet | 270-290 | 220 | methanol | 99.7 | 99.7 |
| Example 13 (comparative) | Cu | $Cr_2O_3$ | $MnO_2$, BaO | powder | 160-175 | 220 | n-butanol | 93.9 | 17.3 |
| Example 14 (comparative) | Cu | $Al_2O_3$ | $MnO_2$ | tablet | 75-90 | 220 | isobutanol | 99 | 64 |
| Example 15 (comparative) | Ru | $Al_2O_3$ | | tablet | 75-90 | 220 | isobutanol | >95 | <5 |
| Polymer and oligomer raw material | | | | | | | | | |
| Example 11 | Cu | $Cr_2O_3$ | $MnO_2$, BaO | powder | 160-175 | 220 | isobutanol | 42.7 | 66.6 |
| Example 12 | Cu | $Cr_2O_3$ | $MnO_2$, BaO | powder | 230-250 | 220 | isobutanol | 100 | 97.8 |

The invention claimed is:

1. A process for hydrogenation of caprolactone and/or its oligomers or polymers to 1,6-hexanediol characterized in that said process is performed in liquid phase at a pressure between 220 and 310 bar and a temperature between 180-240° C., and that said process is performed in the presence of a catalytically effective amount of at least one catalyst comprising Cu, Mn, Al, Cr, Zn, Ba and/or Zr and in the presence of at least one of the solvents methanol, isobutanol and/or 1,6-hexanediol.

2. A process according to claim 1, characterised in that said process is performed in a single reactor.

3. A process according to claim 1, characterised in that said catalyst is present as one or more oxides.

4. A process according to claim 1, characterised in that said catalyst is present as one or more elemental metals.

5. A process according to claim 1, characterised in that said catalyst is present as a combination of one or more oxides and one or more elemental metals.

6. A process according to claim 1, characterised in that said catalyst further comprises a promoter.

7. A process to claim 6, characterised in that said promoter is $MnO_2$, BaO, ZnO, FeO, $Fe_2O_3$, $Fe_3O_4$ and/or a mixture thereof.

8. A process according to claim 1, characterised in that said catalyst is supported on a carrier containing $Al_2O_3$, $SiO_2$, $TiO_2$, activated carbon, $Cr_2O_3$ and/or ZnO and/or CaO.

* * * * *